(12) United States Patent
Briscoe et al.

(10) Patent No.: US 9,226,730 B2
(45) Date of Patent: Jan. 5, 2016

(54) SWEAT COLLECTING DEVICE (71) Applicants: Dennis R. Briscoe, Providence, UT (US); Bryce P. Mc Euen, Providence, UT (US)

(72) Inventors: Dennis R. Briscoe, Providence, UT (US); Bryce P. Mc Euen, Providence, UT (US)

(73) Assignee: ELITechGroup Inc., Logan, UT (US)

( * ) Notice: Subject to any disclaimer, the term of this patent is extended or adjusted under 35 U.S.C. 154(b) by 309 days.

(21) Appl. No.: 13/841,296

(22) Filed: Mar. 15, 2013

(65) Prior Publication Data

US 2014/0276220 A1    Sep. 18, 2014

(51) Int. Cl.
*A61B 10/00*    (2006.01)

(52) U.S. Cl.
CPC .................................. *A61B 10/0064* (2013.01)

(58) Field of Classification Search
CPC ........... A61B 10/0045; A61B 10/0064; A61B 5/4266; A61B 5/14521; A61B 5/6833
See application file for complete search history.

(56) References Cited

U.S. PATENT DOCUMENTS

| | | | |
|---|---|---|---|
| 3,862,627 A | | 1/1975 | Hans |
| 4,190,060 A | * | 2/1980 | Greenleaf et al. ............. 600/573 |
| 4,266,556 A | * | 5/1981 | Barlow et al. .................. 600/573 |
| 4,383,529 A | | 5/1983 | Webster |
| 4,542,751 A | | 9/1985 | Webster et al. |
| 4,756,314 A | * | 7/1988 | Eckenhoff et al. ............. 600/573 |
| 4,821,733 A | * | 4/1989 | Peck .............................. 600/361 |
| 4,960,467 A | * | 10/1990 | Peck ........................... 252/408.1 |
| 5,131,390 A | * | 7/1992 | Sakaguchi et al. ............. 600/346 |
| 5,441,048 A | * | 8/1995 | Schoendorfer ................ 600/346 |
| 6,045,541 A | * | 4/2000 | Matsumoto et al. ........... 604/313 |
| 6,198,953 B1 | * | 3/2001 | Webster et al. ................ 600/345 |
| 6,269,265 B1 | * | 7/2001 | Anderson ......................... 604/20 |
| 6,443,892 B1 | | 9/2002 | Kidwell |
| 7,641,620 B2 | * | 1/2010 | Wingler ......................... 600/562 |
| 8,215,192 B2 | * | 7/2012 | Erez et al. .................... 73/864.33 |
| 2009/0306465 A1 | | 12/2009 | Dudai |
| 2010/0044224 A1 | | 2/2010 | Kataky |
| 2012/0165626 A1 | | 6/2012 | Irina et al. |

OTHER PUBLICATIONS

Sevick; Re-Design of WESCOR© Macroduct© Electrode Cystic Fibrosis Sweat Test; Final Presentation, Apr. 16, 2010; 29 pages (unnumbered).
Gibson et al.; Studies of salt excretion in sweat; The Journal of Pediatrics; Jun. 1963; pp. 855-867; vol. 62, Issue 6; Bethesda, Maryland.
PCT Application No. PCT/US14/30754: Filing date Mar. 17, 2014: Wescor Inc.; International Search Report mailed Jan. 20, 2015.

* cited by examiner

*Primary Examiner* — Max Hindenburg (57) ABSTRACT

A sweat collection device includes an elongate concave sweat-collecting surface at a face thereof for placement over an iontophoresis-stimulated area of a patient's skin to collect sweat and pass it through an axial bore in the concavity. A length of flexible tubing is secured to the axial bore for receiving and storing the collected sweat. A chamber may be provided for holding the tubing in flat coiled condition. Collected sweat builds up within the tubing from the axial bore. The device can include markings to indicate when a minimum amount of sweat has been collected in the tubing and can indicated a range for collected sweat that takes into account variations in the tubing. An open end of the tubing can be flared for easy insertion of a blunt needle to extract sweat or a guide passage can guide insertion of the needle into the open end of the tubing.

20 Claims, 3 Drawing Sheets

SWEAT COLLECTING DEVICE

BACKGROUND

1. Field of the Invention

The present invention relates generally to the collection of human sweat for medical evaluation and is particularly directed to sweat collection devices.

2. Related Art

It is known that the concentrations of sodium and chloride are considerably above normal in the sweat of individuals suffering from cystic fibrosis. Sweat testing is routinely used to diagnose cystic fibrosis, particularly in infants, where such testing is often done between birth and about four weeks of age. In one method of sweat collection, as described in U.S. Pat. No. 4,542,751, incorporated herein by reference, sweating is induced in a substantially flat area of skin by pilocarpine iontophoresis, usually performed using an electrode with a substantially circular pilocarpine containing gel disc, as described in U.S. Pat. No. 4,383,529, incorporated herein by reference, and as manufactured by Wescor, Inc. of Logan, Utah, as a Pilogel® Iontophoresis Disc, placed over the skin of the individual to be tested where sweating is desired. A return electrode is placed on the skin near the electrode with the pilocarpine containing gel disc and a voltage is applied between the electrodes sufficient to cause current flow through the pilocarpine containing gel disc and into the skin between the electrodes. The pilocarpine molecules flow from the pilocarpine containing gel disc through and into the skin area in contact with the pilocarpine containing gel disc. When the pilocarpine iontophresis is complete, the electrodes are removed. The pilocarpine in the circular skin area that was under and in contact with the circular pilocarpine containing gel disc activate the sweat glands in that skin area so that sweating takes place in that skin area.

After removal of the electrodes, a sweat collecting device known as the Macroduct® Sweat Collector, manufactured by Wescor, Inc. of Logan, Utah, which has a concave underside sweat-collecting surface of circular cross section, is placed over the iontophoretically-stimulated area on the skin and the device is firmly strapped in place. Sweat secreted by the individual's sweat glands flows between the skin and the concave underside sweat-collecting surface of the sweat collector and into a micro bore sweat collector tube. After a sufficient volume of sweat has accumulated in the sweat collector tube, the sweat is expelled from the tube and tested for chloride, sodium, and/or total electrolyte content.

While the prior art Macroduct® Sweat Collector described in the above referenced U.S. Pat. No. 4,542,751 works well in collecting sweat from infants for most testing currently being done, producing and collecting enough sweat for some testing is sometimes a problem. Sweat for sweat testing is usually collected from the arm or leg of the patient being tested. Because of the small width of an infant's arm or leg, particularly when four weeks or less of age, the diameter, and therefore the cross sectional area, of the circular cross section of the iontophoresis creating electrode and the circular cross section of the sweat-collecting surface of the sweat collector are limited by the width of the arm or leg. This limits the size of the area of the infant from which sweat can be produced and then collected by the sweat collector.

SUMMARY OF THE INVENTION

It has been found that by elongating the circular cross section of the concave underside sweat-collecting surface of the Macroduct® Sweat Collector, the sweat-collecting surface of the sweat collector will have a larger overall cross sectional area to thereby collect more sweat in a given period of time than does the prior art circular cross section concave undersurface and will still fit the geometry of small limbs of infants. By elongating the circular cross section of the concave underside sweat-collecting surface, the width of the sweat-collecting surface is not increased so as to still fit within the width of the infant's arm or leg, while the length of the sweat-collecting surface along the length of the arm or leg is increased, but since the length of the arm or leg is normally greater than the width of the arm or leg, will still comfortably fit on a substantially flat portion of the arm or leg. However, increasing the cross sectional area of the sweat-collecting surface of the sweat collector will increase the amount of sweat collected only if sweat is being produced by the increased area of the skin covered by the increased area of the sweat-collecting surface. Therefore, when a pilocarpine iontophoresis system is being used to produce the area of sweating, such system has to produce sweating in the increased area of sweat collection. If the pilocarpine iontophoresis system of the referenced U.S. Pat. No. 4,383,529 is used in conjunction with the sweat collector of the invention, the electrode with the pilocarpine containing gel disc and the pilocarpine containing gel disc used should have an elongated cross sectional configuration and area at least about equal to the elongated cross sectional configuration and area of the sweat-collecting surface of the sweat collector. When using a sweat collector with the elongated sweat-collecting surface, a similarly elongated pilocarpine containing disc will be used for the pilocarpine iontophoresis so that sweating is induced in substantially all of the skin covered by the sweat-collecting surface of the sweat collector.

Thus, according to the invention, a sweat collection device for application to a substantially flat area of the human body comprises a solid body having a face thereof forming an elongate concave sweat-collecting surface which gradually recedes from a rim lying wholly in a common plane to an axial bore that extends to the opposite face of the solid body, the maximum depth of the concave means being such that the skin and flesh of the flat area of a human body to which the device is applied will bulge into contact with the sweat-collecting surface over substantially the entire area thereof when the rim is placed firmly against the skin of the flat area of the human body, leaving substantially no dead space in the interface between the bulged skin and the sweat-collecting surface, whereby body secretion pressure of sweat will force the sweat along the sweat-collecting surface to and through the axial bore. The axial bore is adapted to connect with a length of flexible, sweat collector tubing at the opposite face of the solid body, and the solid body is adapted to be fastened against the flat area of a human body from which sweat is to be collected so as to maintain firm placement of said rim and sweat-collecting surface against the skin.

In further improving the prior art device, the free open end of the sweat collector tubing may be flared to more easily receive a small syringe or blunt needle for use in removal of sweat from the sweat collector tubing. Alternately, a guide passage may be provided in the sweat collector body to extend through the body from the chamber for receiving the flexible sweat collector tubing to outside the sweat collector body. The guide passage can have a tapered entrance from outside the body so can easily receive the end of a small syringe or blunt needle and the guide passage will guide the needle into the open end of the sweat collector tubing.

Further, since the inside diameter of the sweat collector tubing which is usually formed by extrusion is subject to small variations within the manufacturing tolerance for the tubing, the volume of sweat collected within a fixed length of the tubing is subject to small variations. Therefore, the collector tubing or device holding the collector tubing may be marked to indicate when sufficient sweat has been collected for the desired testing. Such indication, in addition to indicating when a sufficient amount of sweat has definitely been collected taking into account the potential variations in the extruded cross sectional area of the tubing, can also identify the range of volume of sweat collected in the collector tube that, taking into account the potential variations in the extruded cross sectional area of such tubing, may be sufficient for testing, or may not be sufficient for testing.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

In the illustrated example embodiment as shown in FIGS. 1-4, similarly to the sweat collector shown in referenced prior art U.S. Pat. No. 4,542,751, the device of the invention comprises a sweat collector body 9 advantageously molded to shape from a suitable plastic material, such as polyethylene or polystyrene, and including a sweat collecting portion 10 projecting integrally from a back portion formed as a backing plate 11 provided with slot-like openings 12 at opposite sides thereof for the reception of straps 16 constituting means for attaching the device to a person. However, sweat collecting portion 10 projecting integrally from backing plate 11, rather than being of disc formation as in U.S. Pat. No. 4,542,751, is of elongate formation with the axis of elongation being substantially parallel to the slot-like openings 12.

The face of sweat collecting portion 10 has a shallow concavity 13 whose rim 14 lies wholly in a common plane and which is defined by a broad, sweat-collecting, concave surface 15. Concavity 13 is of squat formation, having a broad base and very short altitude. Rim 14 of concavity 13 may include a flat peripheral width around the concave surface 15 or may merely be the edge of the concave sweat-collecting surface 15.

Such concave face of sweat-collecting portion 10 is adapted to be placed and held firmly against the surface of a patient's skin by a size-adjustable strap 16, whose ends are secured in slots 12. A coiled length of flexible, sweat-collector tubing 17 is shown as having one of its ends fitted into or otherwise connected to an axial bore 18, which extends axially through the body portion 10 and communicates with concavity 13 at the apex of concave, sweat-collecting surface 15. The other end of sweat-collector tubing 17 is normally open to allow air to escape as sweat flows into the tubing.

In the illustrated embodiment, provision is made for retention of sweat-collector tubing 17 in compactly coiled form in the back of the sweat collector body 9 by recessing backing plate portion 11 in the form of a circular receiving chamber 19 overlying a portion of sweat-collecting surface 15. Sweat collector tubing 17 is coiled in flat spiral formation and placed in the receiving chamber 19.

Figure 1:
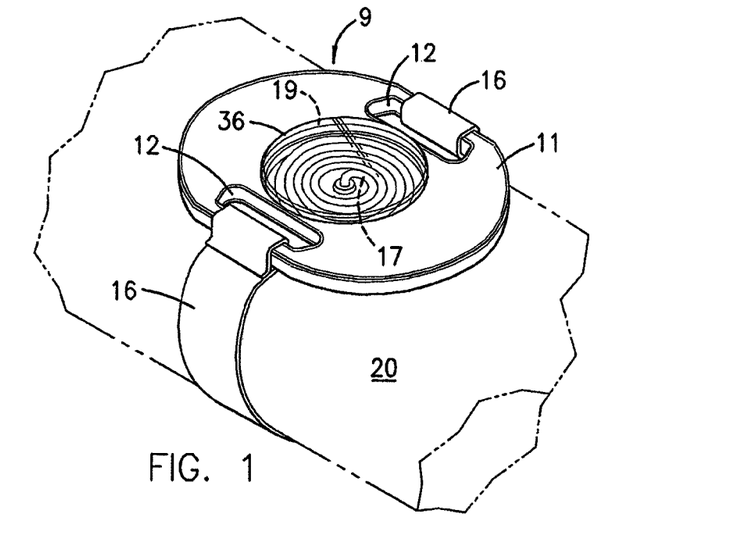
FIG. 1, is a pictorial view of the sweat collecting device of the invention showing the device secured to the forearm, shown fragmentarily in broken lines, of a patient.
Figure 2:
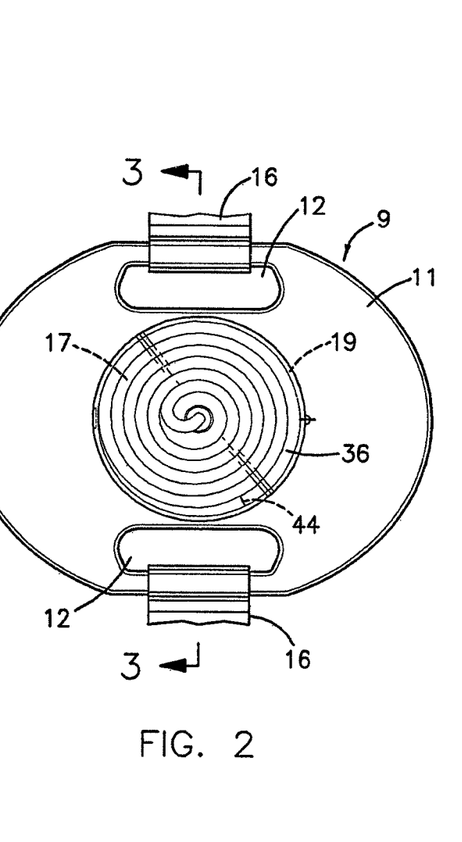
FIG. 2, a top plan view of the device of FIG. 1.

Sweat is generally collected from the fleshy underside of a patient's forearm or from the fleshy portion of the patient's inner thigh. FIG. 1 shows the sweat collector secured to a patient's forearm 20. For convenient application to the limb, strap 16 is preferably provided as two separate lengths with means for adjustment, such as by having mating pieces of hook and loop fastener material, such as "Velcro", applied to overlapping ends thereof. When the device is in place on a patient's skin, the skin and underlying flesh bulge into the concavity 13 against sweat-collecting surface 15.

Prior to placing the device on a patient's skin, the skin over which the device is to be placed is treated to induce sweat production. This treatment will usually be with an iontophoretic electrode, i.e., an electrode containing an ionic drug source, such as pilocarpine, placed against the skin to be treated, with a second return electrode placed against the skin near the iontophoretic electrode so that when a voltage is applied between the electrodes, a current will pass through the skin between the electrodes causing the ionic pilocarpine drug molecules to migrate through the skin in contact with the iontophoretic electrode. Such an iontophoretic electrode may be as shown in referenced prior art U.S. Pat. No. 4,383,529 with the ionic drug source being a pilocarpine containing gel disc as disclosed in that patent. After iontophoresis is completed, the electrodes are removed and the concave sweat-collecting surface 15 of the sweat collecting device is placed over the skin where the iontophoretic electrode had been. The pilocarpine under the skin stimulates the sweat glands to produce sweat for an extended period of time which sweat is then collected by the sweat collecting device. However, for use with the sweat collecting device of the current invention, the iontophoretic electrode including the preformed pilocarpine containing gel disc will have substantially the same elongated shape and size as the shape and size of the elongated sweat-collecting surface of the sweat collecting device of the current invention.

The concavity 13 backed by the concave, sweat-collecting surface 15 is so shallow as to place the area of skin covered thereby in contact with the sweat-collecting surface 15 over substantially the entire area of the sweat-collecting surface 15 without leaving dead space. In this way, sweat, under the pressure at which it is secreted from the sweat glands, is able to rapidly travel across the interface of the skin and collecting surface 15 toward, into, and through axial bore 18, so that substantially all of the sweat is collected in the flexible sweat-collector tubing 17. Pressure of the collecting surface and rim of the device against the skin should be only that which will effect firm placement against the skin. Excessive tightening of strap 16 is neither necessary nor desirable. Four symmetrically positioned, relatively short and outwardly tapered, radial ribs 22 formed integrally with sweat collector body 9 protrude into concavity 13 as barriers to soft skin and flesh blocking the entrance to axial bore 18. Rather than protruding ribs, recesses could be similarly provided for the same purpose.

In the embodiment illustrated, a maximum width of the elongate open base of concavity 13 of twenty-seven (27) millimeters and length of about forty (40) millimeters, with a depth of about one (1) millimeter at the apex, i.e. for the altitude of the elongate squat formation, has been found to be satisfactory, along with collector tubing 17 having an inside diameter of about 0.86 millimeters. While these measurements are satisfactory, the measurements can vary. For example, the concavity could have a depth or altitude substantially in the range of from about one-half (0.5) millimeter to about one and three-quarters (1.75) millimeters, a width substantially in the range of about fifteen (15) millimeters to about thirty five (35) millimeters, and a length substantially in the range of about twenty (20) millimeters to about seventy (70) millimeters, with a length-to-width ratio from about one and three-tenths (1.3) to about two (2). The important considerations in determining dimensions are that the depth or altitude should be small enough to prevent significant dead space between the sweat-collecting surface and the bulged skin, that the width is small enough to fit the width of the limb of the expected patient, such as a new born infant between birth and about four weeks of age, and the length is great enough to provide a sweat-collecting surface area that, in most cases, will easily produce enough sweat for valid sweat testing within the time of expected induced sweat production, usual no more than about thirty minutes.

In use of the device having the example dimensions indicated above, it has been found that about one minute elapses from the time the device is strapped onto an area of the patient's skin that has been stimulated by iontophoretic application of pilocarpine, until sweat appears in collector tubing 17. Once sweat appears, it is possible to see the meniscus of sweat advance in the tubing. If desired, markings may be provided to indicate the approximate volume of sweat collected. However, since the inside diameter of the sweat collector tubing which is usually formed by extrusion is subject to small variations within the manufacturing tolerance for the tubing, the volume of sweat collected within a fixed length of the tubing is subject to small variations. Therefore, it is not usually possible to provide a mark on the tubing that will indicate the volume of sweat actually collected within the accuracy required for sweat testing for cystic fibrosis within the standards of the Cystic Fibrosis Foundation. The volume of sweat tested from the volume of sweat collected will need to be measured by more accurate means, such as by weighing. However, the sweat collector tube or the device holding the sweat collector tube may be marked to identify the range of volume of sweat collected in the sweat collector tube which will provide a sufficient minimum sample of sweat for sweat testing when taking into account the potential variations in the extruded cross sectional area of such tubing.

Typically, a volume of about eight or more microliters of sweat is required for analysis by titration or electrical conductivity methods. However, it is desirable to collect an excess of sweat for ease in handling and to allow the analysis to be repeated so as to average out any deviation in salt concentration caused either by variations in the amount of salt contained in various portions of the excreted sweat or by external factors. Further, it is important that the sweat collected is excreted by the body at a minimum rate to provide reliable cystic fibrosis diagnostic results under Cystic Fibrosis Foundation guidelines. Under current Cystic Fibrosis Foundation guidelines this rate is at least 1 $gm/m^2/min$. This minimum collection rate will produce fifteen microliters of sweat in thirty minutes for a collection area of five $cm^2$ and proportionately more or less for larger or smaller collection areas.

Figure 5:
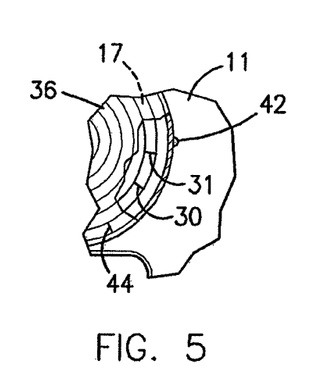
FIG. 5, a fragmentary top plan view of the lower right hand portion of the receiving recess for the sweat collector tubing in the sweat collecting device showing sweat collector tubing coiled therein, and showing markings on the sweat collector tubing to show a range of volume of sweat collected in the sweat collector tubing.

In order to ensure enough sweat is obtained and that it is obtained at least at the minimum rate, it is advantageous to provide an indication when a minimum desirable volume of sweat, such as, for example, fifteen microliters of sweat, has been obtained in the sweat collector tubing. As indicated, the inside diameter of the sweat collector tubing, which is usually formed by extrusion, is subject to small variations within the manufacturing tolerance for the tubing so the volume of sweat collected within a fixed length of the tubing is subject to small variations (the volume of sweat collected is determined by the area of the inside collector tubing passage, determined by the inside diameter of the tubing, times the length of the tubing containing sweat). However, the tolerance of the inside diameter of the tubing is usually known. Therefore, using the minimum inside diameter that might be present within the manufacturing tolerance of the tubing, the maximum length for the minimum desired volume of sweat to be collected in the tubing can be determined, and marked, for example, mark 30 on the collector tubing 17 in FIG. 5. When sweat has been collected to this mark 30 indicating collection to maximum length of tubing necessary to provide the minimum desired volume of sweat, it is ensured that regardless of the variation of the diameter of the tubing within manufacturing tolerances, the minimum desired volume of sweat has been collected and collection can stop. The maximum inside diameter of the sweat collector tube that might be present within the manufacturing tolerance of the tubing will provide the minimum length for a set volume of sweat to be collected in the tubing, such as the minimum desired volume of sweat, and can be determined, and marked, for example mark 31 on the tubing 17 in FIG. 5. This will provide two markings, such as markings 30 and 31, along sweat-collector tubing 17 as shown in FIG. 5. If the sweat collected has not reached the minimum length indicated by mark 31, the minimum volume of sweat has definitely not been collected. If the sweat collected in the tubing is between the marks 30 and 31, the minimum volume of sweat may have been collected depending upon the inside diameter of the collector tube. Further measurement of the volume of sweat is necessary to determine the actual volume of sweat collected.

As indicated, a maximum sweat collecting time is usually observed during most sweat collecting procedures, such as a maximum sweat collecting time of thirty minutes. This maximum time is usually determined by the minimum amount of sweat that has to be collected, the time required at the minimum sweat excretion rate to obtain the minimum amount of sweat, and the maximum time that induced sweating will usually produce at least the minimum desired rate of sweating. For example, if the maximum sweat collecting time is thirty minutes, and during that time sweating at the minimum rate of 1 gm/m$^2$/min will produce a volume of collected sweat in the tubing of fifteen microliters, mark 31 on tubing 17 in FIG. 5 may be positioned to represent a collected volume of sweat of fifteen microliters if the inside diameter of the tubing is at maximum allowable tolerance and mark 30 may be positioned to represent a collected volume of sweat of fifteen microliters if the inside diameter of the tubing is at minimum allowable tolerance. During use of the device to collect sweat, the concave face of sweat-collecting portion 10 of the device is placed and held firmly against the pilocarpine-treated surface of the patient's skin, such as by size-adjustable strap 16. Timing of the sweat collecting period is immediately started. The progression of the sweat collection can be watched as the leading edge of the collected sweat moves along the sweat-collector tubing. With the marks 30 and 31 positioned as in the manner described above, if the collected sweat moves beyond the mark 30 within the sweat collecting period, it is known that enough sweat has been collected at greater than the minimum collection rate and sweat collection can be stopped at any time. As long as the sweat collected reaches mark 30 within the sweat collecting period, it is know that enough sweat has been collected at the minimum excretion rate. If the collected sweat has not reached mark 31 within the sweat collecting period, it is known that the desired amount of sweat has not been collected and that sweating has not been maintained at the minimum rate during the collection period. In such case, it is generally necessary to redo the sweat collection procedure to provide the necessary amount of sweat for acceptable cystic fibrosis testing. If the collected sweat is between marks 30 and 31, it is not known whether or not a sufficient amount of sweat has been collected and the determination of the actual amount of sweat collected, which is generally measured as part of the testing procedure, will determine whether enough sweat was obtained or whether the sweat collection procedure has to be redone.

Figure 6:
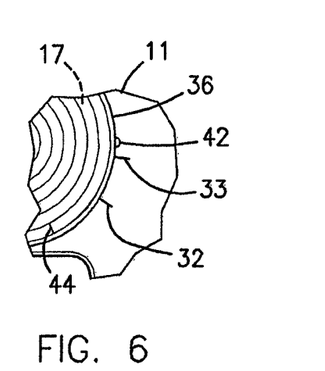
FIG. 6, a fragmentary top plan view of the lower right hand portion of the receiving recess for the sweat collector tubing in the sweat collector device showing sweat collector tubing coiled therein similar to FIG. 5, but showing markings on the sweat collector body to show a range of volume of sweat collected in the sweat collector tubing.

Rather than providing the marks 30 and 31 on the sweat-collecting tubing itself, marks may be provided on the device casing in any location where the desired indication of amount of sweat collected can be determined. For example, marks 32 and 33 may be provided on the back of the back portion 11 adjacent the circular chamber 19 as shown in FIG. 6 to provide a similar indication as marks on the tubing would provide. In the case of marks 32 and 33 in FIG. 6, which shows the same tubing arrangement as shown in FIG. 5, a user would know that the marks 32 and 33 apply to the position of the leading edge of the sweat in the next to the last coil of the tubing coil.

Figure 3:
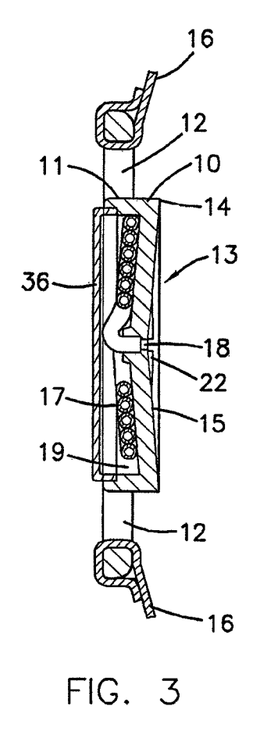
FIG. 3, a vertical section taken on the line 3-3 of FIG. 2.
Figure 4:
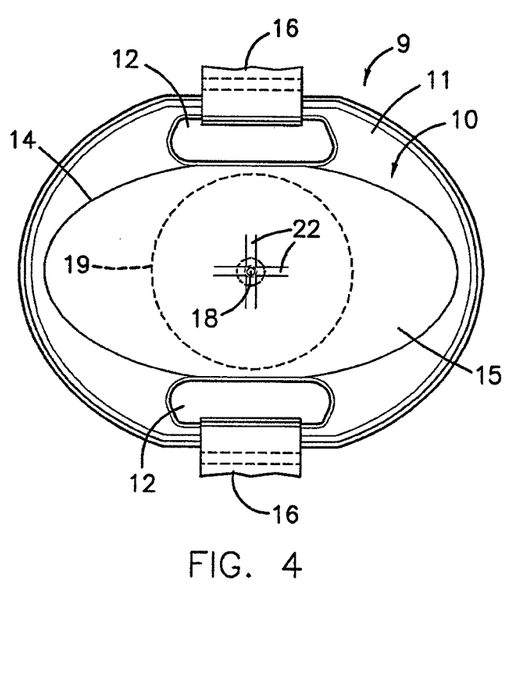
FIG. 4, a bottom plan view of the device of FIG. 1.
Figure 7:
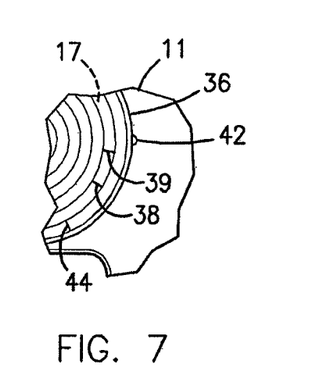
FIG. 7, a fragmentary top plan view of the lower right hand portion of the receiving recess for the sweat collector tubing in the sweat collector device showing sweat collector tubing coiled therein similar to FIG. 5, but showing markings on a cover over the receiving recess to show a range of volume of sweat collected in the sweat collector tubing.

Alternately, where a cover is provided for the chamber 19, such cover 36 being shown in FIGS. 3 and 7, markings 38 and 39, FIG. 7, can be provided on cover 36 over the position of coiled collector tubing 17 to mark the positions similarly as they are shown on the tubing in FIG. 5. With markings 38 and 39 on cover 36, the cover can include a slot, not shown, to interface with tab 42 on back portion 11 so that cover 36 can only be mounted on back portion 11 in one orientation to ensure that the markings 38 and 39 are properly positioned in relation to the coiled sweat collector tubing 17.

With any of the markings described, a red area or other marking can be included between the minimum and maximum marks to remind a used that when the sweat collection ends between those marks, further measurement of the volume of sweat collected is necessary to determine if the minimum volume of sweat has actually been collected.

Once the sweat has been collected in sweat collector tubing 17, the collected sweat has to be removed from the tubing and discharged for measuring a volume for testing and for actual testing of chloride, sodium, and/or total electrolyte content. Generally, in order to remove the sweat from collector tubing 17, collector tubing 17 is disconnected from axial bore 18, either by pulling it free or by severing it at its emergence from such bore. It should be noted that there is a tendency for a vacuum to form between the sweat collecting surface 15 and the skin, so, if the strap 16 is loosened and the device removed with tubing 17 still connected, sweat may be inadvertently withdrawn from the collector tubing and deposited back on the skin. Thus, it is important that the tubing 17 be removed first.

The sweat collected in flexible collector tubing 17 may be expelled or withdrawn and tested in any convenient way. In a commonly used way of expelling the sweat from the sweat collector tubing of the device of referenced U.S. Pat. No. 4,542,751, a small syringe or blunt hypodermic needle is inserted into the open end 44 of the sweat collector tubing 17 and the tubing 17 is then cut where it connects to axial bore 18. As indicated, this is done prior to removing the device from the skin to prevent suction that may be created during removal of the device from the skin from drawing sweat out of the sweat collector tubing. The sweat can then be forced from the tubing for measurement and testing. It has been found difficult with the device of referenced U.S. Pat. No. 4,542,751 for some users to be able to insert the small syringe or blunt needle into the open end 44 of the sweat collector tubing 17. The current invention can provide a flared open end 46, FIG. 8, to allow the small syringe or blunt needle to be more easily inserted into the flared open end 46 of sweat collector tubing 17. Alternatively, as shown in FIG. 9, the open end of the sweat collector tubing 17 can be provided with a flared insert 48 or other fitting to allow the small syringe or blunt needle to be more easily inserted into or otherwise connected to the free end 48 of sweat-collector tubing 17.

Figure 10:
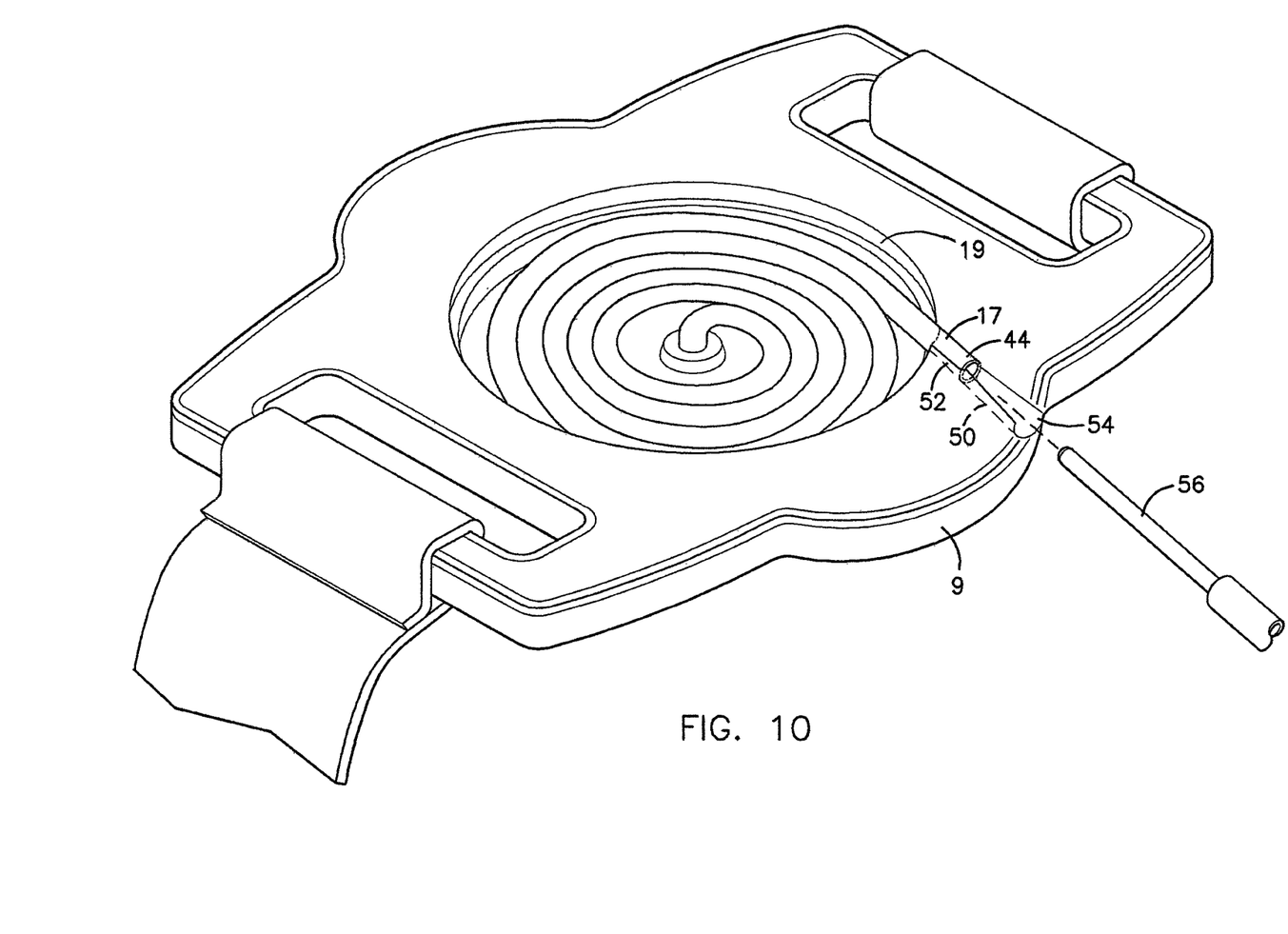
FIG. 10, a pictorial view of a further embodiment of the sweat collecting device of the invention including a guide passage extending from the open end of the sweat collector tubing positioned in the device to the outside of the device for guiding the end of a small syringe or blunt needle into the end of the sweat collector tubing, and showing a slightly different shape for the body of the device.

In a further embodiment shown in FIG. 10, a guide passage 50 is provided in sweat collector body 9 extending through the body from the sweat collector tubing receiving chamber 19 to outside the sweat collector body 9 to guide insertion of a small syringe or blunt needle into the open end 44 of the sweat collector tubing 17. With such arrangement, the end 44 of sweat collector tubing 17 is positioned in sweat collector tubing receiving end 52 of the guide passage 50 with the opposite, tapered end 54 of the guide passage 50 opening to the outside of the collector body 9. The end of a sweat collecting needle 56, such as a small syringe or blunt needle, can be easily inserted into tapered end 54 of guide passage 50 and easily pushed through the guide passage 50 into the open end 44 of tubing 17, which is held in sweat collector tubing receiving end 52 of the guide passage 50. The guide passage can be an open passage as shown, or can be a closed passage. The use of an open passage allows easier insertion and removal of the sweat collector tubing. Again, when sweat collecting needle 56 has been inserted into the end 44 of tubing 17, the tubing should be cut where it connects to axial bore 18 to allow sweat collector tubing 17 to be removed from receiving chamber 19 and the sweat in sweat collector tubing 17 to be removed from the tubing. While FIG. 10 shows a slightly different shape for collector body 9 than shown in the earlier Figs., this merely illustrates that various body shapes can be used for the device. The particular body shape of FIG. 10 is not necessary for use of the illustrated guide passage.

A satisfactory procedure for removal of the sweat from sweat collector tubing 17 when using the guide passage is that once the sweat has been collected in tubing 17, if a protective cover 36 is in place over the receiving chamber 19, remove the protective cover. Insert the sweat collecting needle 56 into tapered end 54 of guide passage 50 and through guide passage 50 into the open end 44 of the sweat collector tubing 17. Guide passage 50 helps in registering the needle correctly with the inside of sweat collector tubing 17. If the sweat hasn't reached the open end 44 of the sweat collector tubing 17 where the needle is inserted, the sweat can be drawn slightly back so that the column of sweat is in the middle of the coiled sweat collector tubing 17 with an air gap at the outer and inner ends. Lift the sweat collector tubing end 44 with the needle (this requires an open guide passage as illustrated) and uncoil the tubing from the collector chamber 19. Clip or cut the tubing near where it extends from the axial bore 18 of the collector body 9. Transfer the sweat sample from the sweat collector tubing 17 to a sealable container for transfer to the testing site, or transfer the sweat sample directly to sweat testing apparatus when such sweat testing apparatus is immediately available for use.

Figure 8:
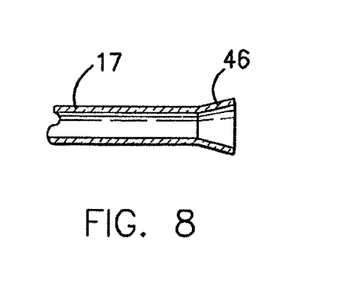
FIG. 8, a fragmentary longitudinal section of the open end portion of the sweat collector tubing showing how the open end of the sweat collector tubing may be flared for easy insertion of a small syringe or blunt needle for use in removal of sweat from the collector tubing.
Figure 9:
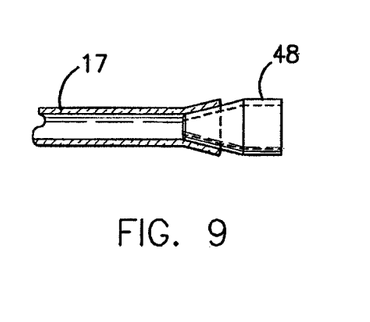
FIG. 9, a fragmentary longitudinal section of the open end portion of the sweat collector tubing similar to that of FIG. 8 showing an insert in the open end of the sweat collector tubing providing the flare for easy insertion of a small syringe or blunt needle.

While the guide passage feature of FIG. 10, the flared open tubing end features of FIGS. 8 and 9, and the inclusion of markings indicating volume of sweat collected in the sweat collector tubing as shown in FIGS. 5, 6, and 7 are all shown in this application in connection with the elongated sweat-collecting surface, such features can be used with the prior art sweat collectors as well.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A sweat-collection device for application to a substantially flat area of the human body, comprising a solid body having a face thereof forming an elongate concave sweat-collecting surface which gradually recedes from a rim lying wholly in a common plane to an axial bore that extends to the opposite face of said solid body, the maximum depth of said concave sweat-collecting surface being such that the skin and flesh of said flat area of a human body to which the device is applied will bulge into contact with said sweat-collecting surface over substantially the entire area thereof when said rim is placed firmly against the skin of said flat area of the human body, leaving substantially no dead space in the interface between the bulged skin and said sweat-collecting surface, whereby body secretion pressure of sweat will force said sweat through said interface to said axial bore, said axial bore being adapted to connect with a length of flexible, sweat collector tubing at said opposite face of the solid body, and said solid body being adapted to be fastened against the said flat area of a human body so as to maintain firm placement of said rim and sweat-collecting surface against the skin.

2. A sweat-collection device according to claim 1, wherein the solid body includes a portion of elongate formation having an elongate axis which projects from a portion formed as a backing plate, said portion of elongate formation forming the elongate concave sweat-collecting surface; and wherein there are means in or on said backing plate for removably receiving an attachment strap.

3. A sweat-collection device according to claim 2, wherein the means in said backing plate for removably receiving an attachment strap are slots through the backing plate on opposite sides of the elongate axis with slot axes substantially parallel to the elongate axis.

4. A sweat-collection device in accordance with claim 1, wherein barrier means are provided at the entrance of the axial bore for preventing unusually soft skin and flesh from protruding into said axial bore.

5. A sweat-collection device in accordance with claim 1, having the opposite face of the solid body recessed as a receiving chamber for receiving flexible sweat collector tubing when connected to the axial bore and coiled in flat formation.

6. A sweat-collection device in accordance with claim 5, including a length of flexible sweat collector tubing having opposite ends and normally connected at one end to the axial bore for collecting sweat therefrom and normally coiled in a flat, spiral formation within the receiving chamber, said opposite end being open, whereby, as sweat is collected by the sweat-collecting device and flows into and through the axial bore, the sweat flows into and collects in the sweat collector tubing, the advancement of the collected sweat being visible as it advances in the sweat collector tubing from the axial bore toward the open end.

7. A sweat-collection device in accordance with claim 6, wherein the open end of the sweat collector tubing is flared.

8. A sweat-collection device in accordance with claim 6, wherein the open end of the sweat collector tubing includes a flared insert.

9. A sweat-collection device in accordance with claim 6, wherein a minimum volume of sweat is to be collected by the device, wherein the sweat collector tubing has a length and an inside diameter, wherein the volume of sweat collected within the sweat collector tubing is dependent upon the length of collected sweat within the sweat collector tubing extending from the axial bore toward the open end, and additionally including a marking positioned with respect to the sweat collector tubing and to the sweat advancing in the sweat collector tubing to be indicative of having collected the minimum volume of sweat within the sweat collector tubing.

10. A sweat-collection device in accordance with claim 9, wherein the inside diameter of the sweat collector tubing can vary over a manufacturing tolerance between a known maximum diameter and a known minimum diameter whereby the volume of sweat collected within a given length of sweat collector tubing is not accurately determined and can vary between a minimum given length volume determined by assuming the minimum diameter is present over the entire given length and a maximum given length volume determined by assuming the maximum diameter is present over the entire given length, and wherein the marking is positioned with respect to the sweat collector tubing and to the sweat advancing in the sweat collector tubing to indicate when the sweat advancing in the sweat collector tubing reaches a given length of sweat collector tubing wherein the minimum volume of sweat to be collected is equal to the minimum given length volume thereby ensuring that at least the minimum volume of sweat to be collected has been collected.

11. A sweat-collection device in accordance with claim 10, wherein the marking is positioned on the sweat collector tubing.

12. A sweat-collection device in accordance with claim 10, wherein the marking is on the sweat-collection device.

13. A sweat-collection device in accordance with claim 12, wherein the sweat-collection device includes a cover over the receiving chamber and the marking is on the cover.

14. A sweat-collection device in accordance with claim 9, wherein the inside diameter of the sweat collector tubing can vary over a manufacturing tolerance between a known maximum diameter and a known minimum diameter whereby the volume of sweat collected within a given length of sweat collector tubing is not accurately determined and can vary between a minimum given length volume determined by assuming the minimum diameter is present over the entire given length and a maximum given length volume determined by assuming the maximum diameter is present over the entire given length, and wherein the marking indicates a range and is positioned with respect to the sweat collector tubing and to the sweat advancing in the sweat collector tubing to indicate at a lower end of the range when the sweat advancing in the sweat collector tubing reaches a given length of sweat collector tubing wherein the minimum volume of sweat to be collected is equal to the maximum given length volume and to indicate at the upper end of the range when the sweat advancing in the sweat collector tubing reaches a given length of sweat collector tubing wherein the minimum volume of sweat to be collected is equal to the minimum given length volume, wherein when the collected sweat enters the range and is within the range, the minimum volume of sweat to be collected may have been collected, but such collection is not ensured, and when the collected sweat reaches the top of the range, collection of the minimum volume of sweat to be collected is ensured.

15. A sweat-collection device in accordance with claim 14, wherein the marking is positioned on the sweat collector tubing.

16. A sweat-collection device in accordance with claim 14, wherein the marking is on the sweat-collection device.

17. A sweat-collection device in accordance with claim 16, wherein the sweat-collection device includes a cover over the receiving chamber and the marking is on the cover.

18. A sweat-collection device in accordance with claim 6, wherein the solid body additionally includes a guide passage extending through the solid body from the chamber for receiving the flexible sweat collecting tubing to outside the solid body, said guide passage having a flexible sweat collector tubing receiving end adjoining the chamber for receiving and holding the open end of the sweat collector tubing coiled in the chamber and a tapered end opening to outside the solid body, said tapered end adapted to receive a sweat collecting needle to be guided by the guide passage into the open end of the sweat collector tubing received in the sweat collector tubing receiving end of the guide passage.

19. A sweat-collection device for application to a substantially flat area of the human body, comprising:
  a solid body having a face thereof forming a concave sweat-collecting surface which gradually recedes from a rim lying wholly in a common plane to an axial bore that extends to the opposite face of said solid body, the maximum depth of said concave sweat-collecting surface being such that the skin and flesh of said flat area of a human body to which the device is applied will bulge into contact with said sweat-collecting surface over substantially the entire area thereof when said rim is placed firmly against the skin of said flat area of the human body, leaving substantially no dead space in the interface between the bulged skin and said sweat-collecting surface, whereby body secretion pressure of sweat will force said sweat through said interface to said axial bore, said bore being adapted to connect with a length of flexible, sweat collector tubing at said opposite face of the solid body, and said solid body being adapted to be fastened against the said flat area of a human body so as to maintain firm placement of said rim and sweat-collecting surface against the skin, the opposite face of the solid body being recessed to form a chamber for receiving flexible sweat collector tubing when connected to the axial bore and coiled in flat formation;
  a length of flexible sweat collector tubing having opposite ends and normally connected at one end to the axial bore for collecting sweat therefrom and normally coiled in a flat, spiral formation within the receiving chamber, said opposite end being open, whereby, as sweat is collected by the sweat-collection device and flows into and through the axial bore, the sweat flows into and collects in the sweat collector tubing, the advancement of the collected sweat being visible as it advances in the sweat collector tubing from the axial bore toward the open end; and
  a guide passage extending through the solid body from the chamber for receiving the flexible sweat collecting tubing to outside the solid body, said guide passage having a flexible sweat collecting tubing receiving end adjoining the chamber for receiving and holding the open end of the sweat collecting tubing coiled in the chamber, and a tapered end opening to outside the solid body, said tapered end adapted to receive a sweat collecting needle to be guided by the guide passage into the open end of the sweat collector tubing received in the sweat collector tubing receiving end of the guide passage.

20. A sweat-collection device for application to a substantially flat area of the human body, comprising:
  a solid body having a face thereof forming a concave sweat-collecting surface which gradually recedes from a rim lying wholly in a common plane to an axial bore that extends to the opposite face of said solid body, the maximum depth of said concave sweat-collecting surface being such that the skin and flesh of said flat area of a human body to which the device is applied will bulge into contact with said sweat-collecting surface over substantially the entire area thereof when said rim is placed firmly against the skin of said flat area of the human body, leaving substantially no dead space in the interface between the bulged skin and said sweat-collecting surface, whereby body secretion pressure of sweat will force said sweat through said interface to said axial bore, said axial bore being adapted to connect with a length of flexible, sweat collector tubing at said opposite face of the solid body, and said solid body being adapted to be fastened against the said flat area of a human body so as to maintain firm placement of said rim and sweat-collecting surface against the skin, the opposite face of the solid body being recessed to form a chamber for receiving flexible sweat collector tubing when connected to the axial bore and coiled in flat formation;
  a length of flexible sweat collector tubing having opposite ends and normally connected at one end to the axial bore for collecting sweat therefrom and normally coiled in a flat, spiral formation within the receiving chamber, said opposite end being open, whereby, as sweat is collected by the sweat-collection device and flows into and through the axial bore, the sweat flows into and collects in the sweat collector tubing, the advancement of the collected sweat being visible as it advances in the sweat collector tubing from the axial bore toward the open end; and wherein the inside diameter of the sweat collector tubing can vary over a manufacturing tolerance between a known maximum diameter and a known minimum diameter whereby the volume of sweat collected within a given length of sweat collector tubing is not accurately determined and can vary between a minimum given length volume determined by assuming the minimum diameter is present over the entire given length and a maximum given length volume determined by assuming the maximum diameter is present over the entire given length, and wherein markings indicate a range and are positioned with respect to the sweat collector tubing and to the sweat advancing in the sweat collector tubing to indicate at a lower end of the range when the sweat advancing in the sweat collector tubing reaches a given length of sweat collector tubing wherein a minimum volume of sweat to be collected is equal to the maximum given length volume and to indicate at the upper end of the range when the sweat advancing in the sweat collector tubing reaches a given length of sweat collector tubing wherein the minimum volume of sweat to be collected is equal to the minimum given length volume, wherein when the collected sweat enters the range and is within the range, the minimum volume of sweat to be collected may have been collected, but such collection is not ensured, and when the collected sweat reaches the top of the range, collection of the minimum volume of sweat to be collected is ensured.

* * * * *